(12) United States Patent
Long

(10) Patent No.: US 12,383,434 B2
(45) Date of Patent: Aug. 12, 2025

(54) TUBELESS ENERGY DRAINAGE DEVICE FOR TRAUMA

(71) Applicant: Dan Long, Changsha (CN)

(72) Inventor: Dan Long, Changsha (CN)

(73) Assignee: Dan Long, Hunan (CN)

( * ) Notice: Subject to any disclaimer, the term of this patent is extended or adjusted under 35 U.S.C. 154(b) by 117 days.

(21) Appl. No.: 18/530,338

(22) Filed: Dec. 6, 2023

(65) Prior Publication Data

US 2024/0099893 A1 Mar. 28, 2024

(30) Foreign Application Priority Data

Dec. 13, 2022 (CN) .......................... 202211596074.7

(51) Int. Cl.
| | | |
|---|---|---|
| *A61F 13/00* | (2024.01) | |
| *A61F 13/01* | (2024.01) | |
| *A61L 15/18* | (2006.01) | |
| *A61L 15/20* | (2006.01) | |
| *A61L 15/26* | (2006.01) | |
| *A61L 15/42* | (2006.01) | |

(52) U.S. Cl.
CPC .. *A61F 13/00063* (2013.01); *A61F 13/01017* (2024.01); *A61F 13/01029* (2024.01); *A61L 15/18* (2013.01); *A61L 15/20* (2013.01); *A61L 15/26* (2013.01); *A61L 15/425* (2013.01); *A61L 2300/418* (2013.01)

(58) Field of Classification Search
None
See application file for complete search history.

(56) References Cited

U.S. PATENT DOCUMENTS

| | | |
|---|---|---|
| 2003/0069552 A1 | 4/2003 | O'Keefe et al. |
| 2004/0015140 A1 | 1/2004 | Shields |
| 2005/0101914 A1 | 5/2005 | Shue et al. |
| 2022/0265476 A1* | 8/2022 | Long ....................... A61M 1/90 |

OTHER PUBLICATIONS

CN 107281640 A translation (Year: 2017).*

* cited by examiner

*Primary Examiner* — Kim M Lewis
(74) *Attorney, Agent, or Firm* — Ming Jiang; OPENPTO US LLC

(57) ABSTRACT

A tubeless energy drainage device for trauma, pertaining to the field of tubeless drainage technology, especially relating to a tubeless energy drainage device for trauma. The device includes energy transmission carriers, lead wires, and a frequency electrical energy generator. The frequency energy resonance generator transmits electrical energy to the energy transmission carriers, activates metal potassium ions on the energy transmission carriers, and creates resonance through conduction of metal ions in a wound covering layer and changing frequency of a wound, thereby achieving retrograde drainage of the wound's own sinus in a drainage area. The device disclosed by the present invention is of great significance for the rapid and full drainage of intractable wounds and battlefield wounds, and the drainage, healing, and pain relief of minute wound fistulas that cannot be tubed.

10 Claims, 1 Drawing Sheet

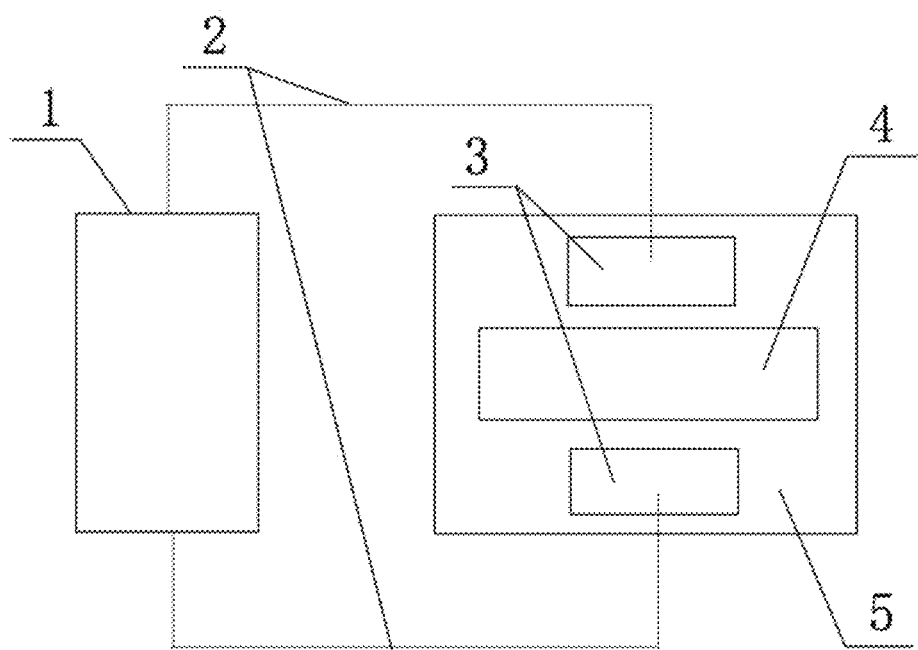

TUBELESS ENERGY DRAINAGE DEVICE FOR TRAUMA

TECHNICAL FIELD

The present invention pertains to the field of tubeless drainage technology, especially relating to a tubeless energy drainage device for trauma.

BACKGROUND

Currently, both domestically and internationally, exudates from sutured wounds and complex distributed minute wound fistulas that cannot be tubed, such as wound fragments, fat particles, metabolites, cannot be effectively drained. Once they enter the bloodstream, they can activate our body's coagulation system, leading to deep vein thrombosis, fat embolism, and even pulmonary embolism, posing a threat to the patient's life. Wound exudates can also cause wound edema, slow wound healing, and scar adhesion tissue formation. Intractable wounds and battlefield wounds are in complex distribution. They cannot be drained if they are opposite the direction of the negative pressure drainage tube, or due to coagulation blocking the tube. Moreover, it is often difficult for doctors to promptly discover blockages within the body's lumens, making it even harder to achieve retrograde drainage. In addition to causing pain and infection, tube placement in patients can also affect rapid healing and recovery, especially in wounds with small, complex fistulas where drainage tubes cannot be placed. Although current prevention guidelines have stopped some venous thrombosis, there is still no effective method in the medical community, both domestically and internationally, for the prevention of postoperative fat embolism. Therefore, there is an urgent need to invent a tubeless energy conduction retrograde drainage device with certain anticoagulant effects, using the sinus tracts of the wounds themselves for rapid and efficient retrograde drainage of fat particles, simultaneously promoting rapid wound healing and providing rapid multimodal analgesia for sensory nerves, thereby saving patients' lives. This has significant importance in the field of surgical operations.

SUMMARY OF THE INVENTION

To address the above problems, the present invention discloses a tubeless energy drainage device for trauma. The technical solution adopted by the present invention is as follows:

A tubeless energy drainage device for trauma includes energy transmission carriers, lead wires, and a frequency energy resonance generator. The frequency energy resonance generator is connected to two energy transmission carriers via the lead wires, and the frequency energy resonance generator transmits electrical energy to the energy transmission carriers, activates metal potassium ions on the energy transmission carriers, and creates resonance through conduction of metal ions in a wound covering layer and changing frequency of a wound, thereby achieving tubeless retrograde drainage of the wound's own sinus and complex minute wound fistulas in the drainage area.

Furthermore, the frequency energy resonance generator includes: a power module, a single-chip control module, an electrical pulse frequency adjustment module, an electrical conduction interference anticoagulation module, and a display module. The single-chip control module regulates and controls the electrical pulse frequency adjustment module, the electrical conduction interference anticoagulation module, and the display module.

Furthermore, the single-chip control module regulates and controls the electrical pulse frequency adjustment module to transmit electrical energy to the energy transmission carriers; the display module, under the control of the single-chip control module, displays working time and a treatment method; the electrical conduction anticoagulation module interferes with blood coagulation of the wound under the control of the single-chip control module.

Furthermore, components constituting the energy transmission carrier include 10% acrylamide, 40% water, 35% glycerin, 5% potassium chloride, 1% sophora, 4% peppermint, and 5% bisacrylamide. The components are mixed and dissolved, then solidified and molded in a mold.

Furthermore, the wound covering layer is provided with the drainage area, and the drainage area is composed of polyurethane foam adhered to the wound covering layer by hot melt adhesive.

Furthermore, the wound covering layer is non-woven fabric or PU film.

Furthermore, in use of the device, the two energy transmission carriers are adhered to the wound covering layer on two sides of the drainage area by hot melt adhesive.

Furthermore, under the regulation and control of the single-chip control module, the electrical pulse frequency adjustment module transmits electrical energy to the energy transmission carriers, activates metal potassium ions on the energy transmission carriers, creates resonance through conduction of metal ions and changing frequency of the wound, thereby maximizing energy and achieving tubeless retrograde drainage of the wound's own sinus through energy release in the wound area and the interference with blood coagulation by the electrical conduction anticoagulation module.

The present invention has the following beneficial effects:

According to the tubeless energy drainage device for trauma disclosed by the present invention, the frequency energy resonance generator is regulated, where the electrical pulse frequency adjustment module, under the control of the single-chip control module, transmits electrical energy to the energy transmission carriers, activates metal potassium ions on the carriers, and creates resonance through conduction of metal ions and changing frequency of the wound, thereby maximizing the conversion of electrical energy into kinetic energy, and achieving tubeless retrograde drainage of the wound's own sinus through energy release in the wound area and the interference with blood coagulation by the electrical conduction anticoagulation module, allowing exudates in the wound area to flow out. This helps in the full and rapid drainage of intractable wounds and battlefield wounds, while electrical energy promotes blood circulation, enabling rapid wound healing and rapid pain relief for nerve conduction anesthesia. This is of great significance for wound healing and pain relief.

DESCRIPTION OF THE DRAWINGS

FIG. 1 is a schematic diagram of a tubeless energy drainage device for trauma according to the present invention.

In the FIGURE, the various signs are: frequency energy resonance generator—1, lead wire—2, energy transmission carrier—3, drainage area—4, and wound covering layer—5.

DESCRIPTION OF EMBODIMENTS

For better understanding the technical solution of the present invention, the following gives a detailed description of the embodiments of the present invention with reference to the accompanying drawings.

As shown in the FIGURE, FIG. 1 is a schematic diagram of a tubeless energy drainage device for trauma according to the present invention. The tubeless energy drainage device includes energy transmission carriers 3, lead wires 2, and a frequency energy resonance generator 1. The frequency energy resonance generator 1 is connected to two energy transmission carriers 3 via the lead wires 2, and the frequency energy resonance generator 1 transmits electrical energy to the energy transmission carriers 3, activates metal potassium ions on the energy transmission carriers 3, and creates resonance through conduction of metal ions in a wound covering layer 5 and changing frequency of a wound, thereby achieving retrograde drainage of the wound's own sinus in a drainage area 4.

The frequency energy resonance generator 1 includes: a power module, a single-chip control module, an electrical pulse frequency adjustment module, an electrical conduction interference anticoagulation module, and a display module. The single-chip control module regulates and controls the electrical pulse frequency adjustment module, the electrical conduction interference anticoagulation module, and the display module.

The single-chip control module regulates and controls the electrical pulse frequency adjustment module to transmit electrical energy to the energy transmission carriers; the display module, under the control of the single-chip control module, displays working time and a treatment method; the electrical conduction anticoagulation module interferes with blood coagulation of the wound under the control of the single-chip control module.

Components constituting the energy transmission carrier 3 include 10% acrylamide, 40% water, 35% glycerin, 5% potassium chloride, 1% sophora, 4% peppermint, and 5% bisacrylamide. The components are mixed and dissolved, then solidified and molded in a mold to produce a block-shaped energy transmission carrier 3, which is then adhered to the wound covering layer 5 by hot melt adhesive.

The wound covering layer 5 is provided with the drainage area 4, and the drainage area 4 is composed of polyurethane foam adhered to the wound covering layer 5 by hot melt adhesive. The wound covering layer 5 is non-woven fabric or PU film.

In use of the device, the two energy transmission carriers 3 are adhered to the wound covering layer 5 on two sides of the drainage area 4 by hot melt adhesive. Under the regulation and control of the single-chip control module, the electrical pulse frequency adjustment module transmits electrical energy to the energy transmission carriers 3, activates metal potassium ions on the energy transmission carriers 3, and creates resonance through conduction of metal ions and changing frequency of a wound, thereby maximizing the conversion of electrical energy into kinetic energy and achieving tubeless retrograde drainage of the wound's own sinus through energy release in the wound area and the interference with blood coagulation by the electrical conduction anticoagulation module, allowing exudates in the surgical area to flow out. This is helpful for the full and rapid drainage of intractable wounds and battlefield wounds, while electrical energy promotes blood circulation, enabling rapid wound healing and rapid pain relief for nerve conduction anesthesia.

The above has further explained the embodiments of the present invention with reference to the drawings, but the present invention is not limited to the described embodiments. For those skilled in the art, various changes, modifications, substitutions, and variations can be made to these embodiments without departing from the principles and spirit of the present invention, and they still fall within the scope of the present invention's protection.

What is claimed is:

1. A tubeless energy drainage device for trauma, characterized in that: the device comprises energy transmission carriers (3), lead wires (2), and a frequency energy resonance generator (1), the frequency energy resonance generator (1) is connected to two energy transmission carriers (3) via the lead wires (2), and the frequency energy resonance generator (1) transmits electrical energy to the energy transmission carriers (3), activates metal potassium ions on the energy transmission carriers (3), and creates resonance through conduction of metal ions in a wound covering layer (5) and changing frequency of a wound, thereby achieving tubeless retrograde drainage of the wound's own sinus in a drainage area (4).

2. The tubeless energy drainage device for trauma according to claim 1, characterized in that: the frequency energy resonance generator (1) comprises: a power module, a single-chip control module, an electrical pulse frequency adjustment module, an electrical conduction interference anticoagulation module, and a display module, wherein the single-chip control module regulates and controls the electrical pulse frequency adjustment module, the electrical conduction interference anticoagulation module, and the display module.

3. The tubeless energy drainage device for trauma according to claim 2, characterized in that: the single-chip control module regulates and controls the electrical pulse frequency adjustment module to transmit electrical energy to the energy transmission carriers; the display module, under the control of the single-chip control module, displays working time and a treatment method; the electrical conduction anticoagulation module interferes with blood coagulation of the wound under the control of the single-chip control module.

4. The tubeless energy drainage device for trauma according to claim 1, characterized in that: components constituting the energy transmission carrier (3) comprise 10% acrylamide, 40% water, 35% glycerin, 5% potassium chloride, 1% sophora, 4% peppermint, and 5% bisacrylamide, wherein the components are mixed and dissolved, then cured and molded in a mold.

5. The tubeless energy drainage device for trauma according to claim 4, characterized in that: the wound covering layer (5) is provided with the drainage area (4), and the drainage area (4) is composed of polyurethane foam adhered to the wound covering layer (5) by hot melt adhesive.

6. The tubeless energy drainage device for trauma according to claim 5, characterized in that: the wound covering layer (5) is non-woven fabric or PU film.

7. The tubeless energy drainage device for trauma according to claim 1, characterized in that: the wound covering layer (5) is provided with the drainage area (4), and the drainage area (4) is composed of polyurethane foam adhered to the wound covering layer (5) by hot melt adhesive.

8. The tubeless energy drainage device for trauma according to claim 5, characterized in that: the wound covering layer (5) is non-woven fabric or PU film.

9. The tubeless energy drainage device for trauma according to claim 7, characterized in that: in use of the device, the two energy transmission carriers (3) are adhered to the wound covering layer (5) on two sides of the drainage area (4) by hot melt adhesive.

10. The tubeless energy drainage device for trauma according to claim 9, characterized in that: under the regulation and control of the single-chip control module, the electrical pulse frequency adjustment module transmits electrical energy to the energy transmission carriers (3), activates metal potassium ions on the energy transmission carriers (3), and creates resonance through conduction of metal ions and changing the frequency of the wound, achieving tubeless retrograde drainage of the wound's own sinus through release of energy in the wound area and interference with blood coagulation by the electrical conduction anticoagulation module.

\* \* \* \* \*